(12) United States Patent
Baek

(10) Patent No.: US 10,528,703 B1
(45) Date of Patent: Jan. 7, 2020

(54) MEDICAL LABELING SYSTEM AND METHOD OF USE

(71) Applicant: Peter S. Baek, Southlake, TX (US)

(72) Inventor: Peter S. Baek, Southlake, TX (US)

(*) Notice: Subject to any disclaimer, the term of this patent is extended or adjusted under 35 U.S.C. 154(b) by 111 days.

(21) Appl. No.: 15/091,188

(22) Filed: Apr. 5, 2016

Related U.S. Application Data

(60) Provisional application No. 62/152,116, filed on Apr. 24, 2015.

(51) Int. Cl.
| | | |
|---|---|---|
| *G06F 19/00* | (2018.01) | |
| *H04N 1/00* | (2006.01) | |
| *G06K 15/02* | (2006.01) | |

(52) U.S. Cl.
CPC ........ *G06F 19/3462* (2013.01); *G06F 19/326* (2013.01); *G06K 15/024* (2013.01); *H04N 1/00334* (2013.01); *H04N 1/00342* (2013.01); *H04N 2201/0082* (2013.01)

(58) Field of Classification Search
CPC ............ G06F 19/3462; G06F 19/3456; G06F 15/024; G06K 2017/009; A61J 2205/30
USPC ........................................................ 705/2–3
See application file for complete search history.

(56) References Cited

U.S. PATENT DOCUMENTS

| | | | | |
|---|---|---|---|---|
| 8,639,525 | B2* | 1/2014 | Levine .................. | G06F 19/326 705/2 |
| 2009/0204255 | A1* | 8/2009 | Yuyama ............... | G06Q 10/087 700/225 |
| 2013/0092727 | A1* | 4/2013 | Edwards ............ | B65C 11/0289 235/375 |
| 2014/0226180 | A1* | 8/2014 | Alex .................. | H04N 1/00519 358/1.15 |
| 2015/0034713 | A1* | 2/2015 | Jones ....................... | G06K 7/10 235/375 |
| 2015/0249770 | A1* | 9/2015 | Delaney ................ | G06F 3/1238 358/3.28 |

* cited by examiner

*Primary Examiner* — Joy Chng
(74) *Attorney, Agent, or Firm* — Richard Eldredge

(57) ABSTRACT

A labeling system for creating labels for medicine containers. The system includes a label printer having an interior area configured to carry a plurality of printing sheets therein; a scanner in data communication with the label printer, the scanner having a reader to scan a drug administer barcode and a drug barcode; and a label sheet printed by the label printer, the label sheet having a plurality of labels adhesively bonded thereto, the label printer being configured to print onto the plurality of labels data information scanned from the administrator barcode and the drug barcode. The label sheet includes a first section for a drug name; a second section for a dosage; a third section for a time and a date; and a fourth section for information related to the drug administer.

15 Claims, 7 Drawing Sheets

MEDICAL LABELING SYSTEM AND METHOD OF USE

BACKGROUND

1. Field of the Invention

The present invention relates generally to printing systems, and more specifically, to a printing system configured to print a plurality of labels for medicine containers.

2. Description of Related Art

It is known that anesthesiologist, doctors, nurses, and the like administer some of the deadliest medications to the patient during operation and recover. The drug administers sometimes work alone without consultations from other parties prior to and during the operation. Prior to the operation, conventional process of preparing the medications for operation includes handwriting the medicine type, dosage, date, and time are written on a wax-type paper. This process 101 is shown in FIG. 1, wherein the drug administer writes on an adhesively-backed wax label 103, which is then placed on the outer surface of the medicine bottle 105.

Conventional labeling methods, as depicted in FIG. 1, suffer from many drawbacks, and have limited reliability due primary to human error. For example, sloppy handwriting can make the label difficult to read, or altogether illegible. It should also be understood that each administer who prepares the label may also be doing so in a manner different from other administers, or attribute different meanings to the content of a label than another administers. This process is widely known and a common problem among anesthesiologist.

Accordingly, there is a need in the art for a labeling system compliant with medical standards that reduces, if not eliminates, human error during the labeling process.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
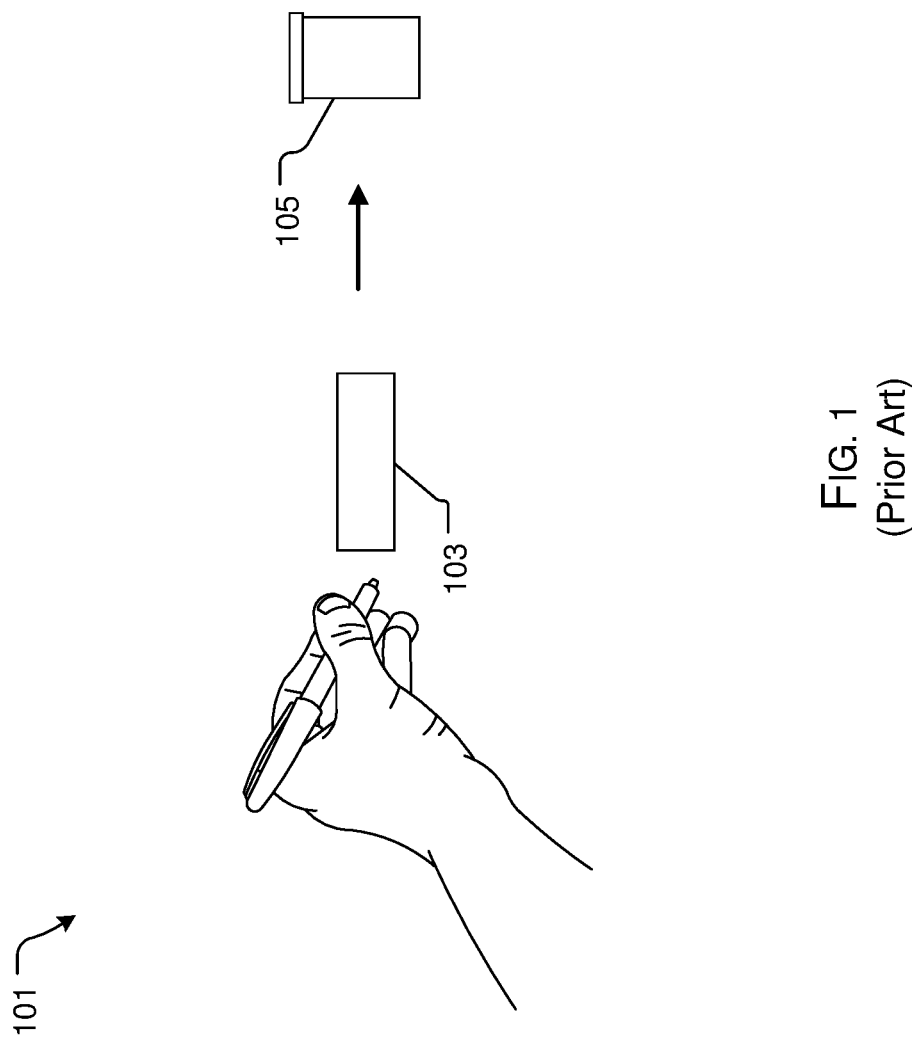
FIG. 1 is a simplified front schematic of a conventional process to create labels for medical containers.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional systems and methods of creating labels for medicine containers. Specifically, the system provides rapid and effective means to create and print a plurality of labels simultaneously, which in turn greatly reduces the time and effort to prepare the medicines for operation. The system and method also reduces, if not eliminates, human error due to legibility of the labels. The system is also adapted for use with a preprinted sheet of barcodes associated with a specific type of drug to be administer, which are scanned by the administer and the drug information printed on a sheet of labels. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
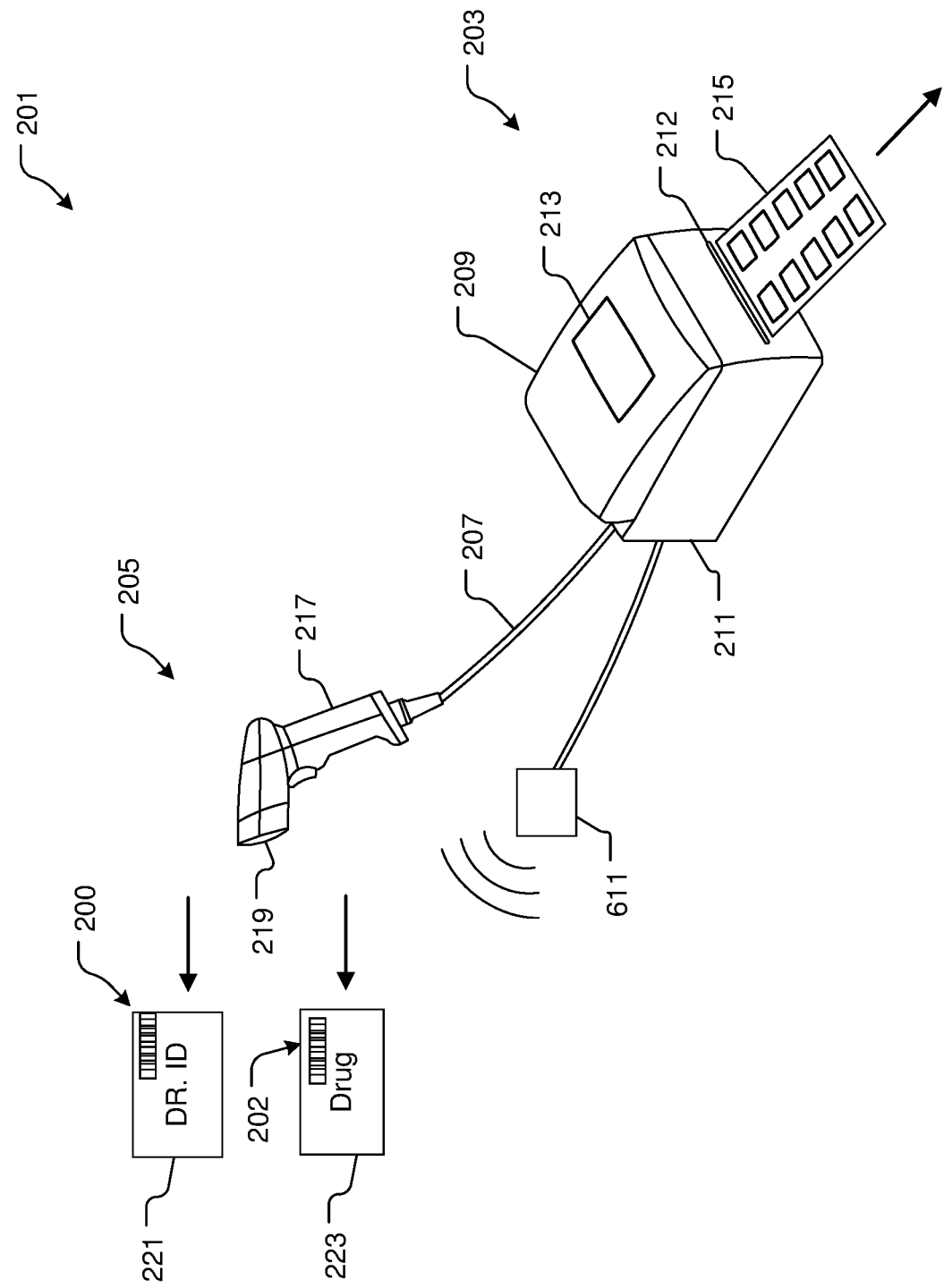
FIG. 2 is an oblique view of a labeling system in accordance with a preferred embodiment of the present application.

Referring now to the drawings wherein like reference characters identify corresponding or similar elements throughout the several views, FIG. 2 depicts an oblique view of a labeling system 201 in accordance with a preferred embodiment of the present application. It will be appreciated that the labeling system 201 overcomes one or more of the above-listed problems commonly associated with the conventional devices and methods for creating labels for medical containers, as will be discussed more fully below.

In the contemplated embodiment, system 201 includes a printer 203 operably associated with a scanner 205 and conductively connected thereto via a cord 207. Printer 203 includes a top 209 pivotally connected to a base 211 configured to carry a plurality of label sheets 215 therein. During use, the user can pivot open top 209 to position label sheets 215 within a cavity (not shown) formed by base 211. The label sheets 215 are fed through a printing device (not shown) disposed within base 211 and exit through an opening 212 where they are then accessible to the user.

Printer 203 is further provided with a display 213 carried on top 209 and in viewing access to the user. In one contemplated embodiment, the display 213 merely displays information related to creating the labels, for example, Doctor Information, medicine information, date, time, dosage, expiration, and so forth. In an alternative embodiment, display 213 is manipulated by the user, for example, the display is touch sensitive, thereby allowing the user to manually input information. The display 213 could also be configured to read finger prints for security verification prior to use.

Although not shown, printer 203 includes one or more ports that allows communication with a computer for preprogramming. Also, in the contemplated embodiment, the printer 203 includes a power cord (not shown) that provides electrical energy to printer 203 via an electrical outlet.

One of the unique features believed characteristic of system 201 is the use of a scanner 205 used to obtain information for printing the labels on sheet 215. This features greatly reduces the time and effort to create medical labels for containers, and potentially eliminates the human error during the process.

Figure 8:
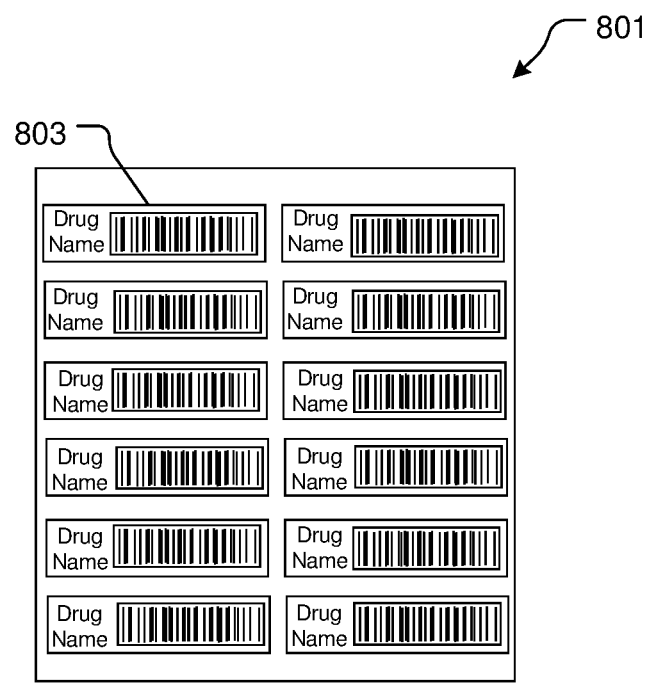
FIG. 8 is a front view of a drug identifier sheet.

Scanner 205 includes a handle 217 integrally attached to a reader 219. During use, the user will hold handle 217 and scan, for example, a barcode 200 associated with the doctor's identification 221 and a barcode 202 associated with the type of medicine being used, as indicated by box 223. It should be understood that the majority of medicine bottles include barcodes adhered to the bottle, which provide important medical information. Thus, box 223 could represent a barcode directly from the medicine bottle. Further, it is contemplated obtaining the drug information from a sheet 801 of labels having different types of drug information, as depicted in FIG. 8.

Figure 3:
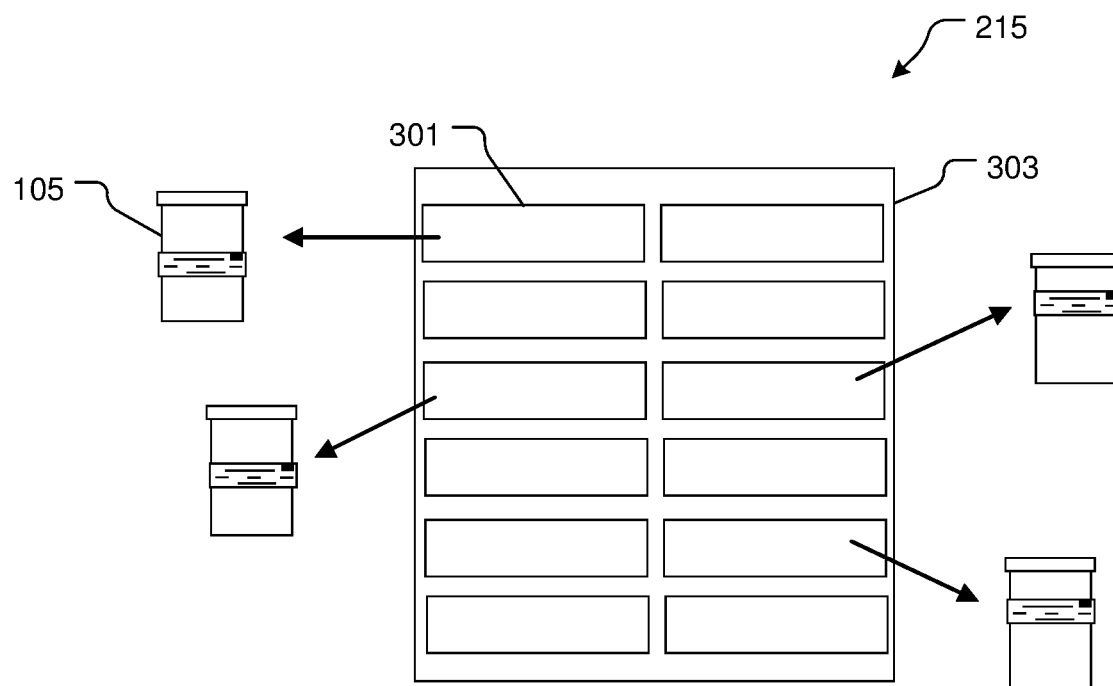
FIG. 3 is a front view of a label sheet of the labeling system of FIG. 2.

Referring now to FIG. 3, a simplified front view of a label sheet 215 is shown having a plurality of medical labels 301 adhesively bonded to a sheet 303. Another unique feature believed characteristic of system 201 is the ability to print a plurality of labels 301 simultaneously, thereby greatly reducing the time and effort to create the labels. During use, a plurality of label sheets 215 are placed in the cavity of base 211 and thereafter fed through a printer device and the drug and doctor information from scanner 205 is placed on individual labels 301. The user then removes labels 301 from sheet 303 and adhesively adheres the labels to bottles 105. In some embodiments, the label sheet could include one or more labels 301 that are blank, which in turn the user can handwrite information directly to the labels 301.

Figure 4:
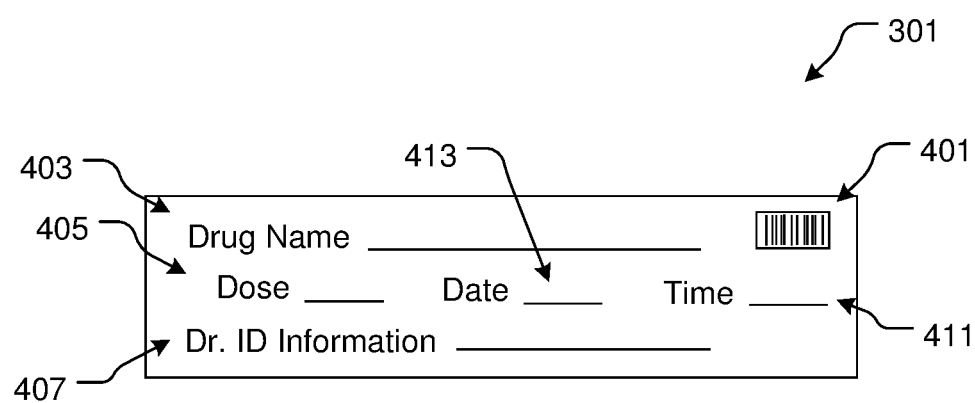
FIG. 4 is a front view of a medical label of the label sheet of FIG. 3.

As depicted in FIG. 4, subject matter such as the Doctor's information, medicine information, dosage, time, date, and an optional bar code can be printed to the label 301 via printer 203. Specifically, the label 301 includes a barcode printed on section 401, the drug name printed on section 403, the dose printed on section 405, the administers information printed on section 407, the time printed on section 411, and the date printed on section 413.

Figure 5:
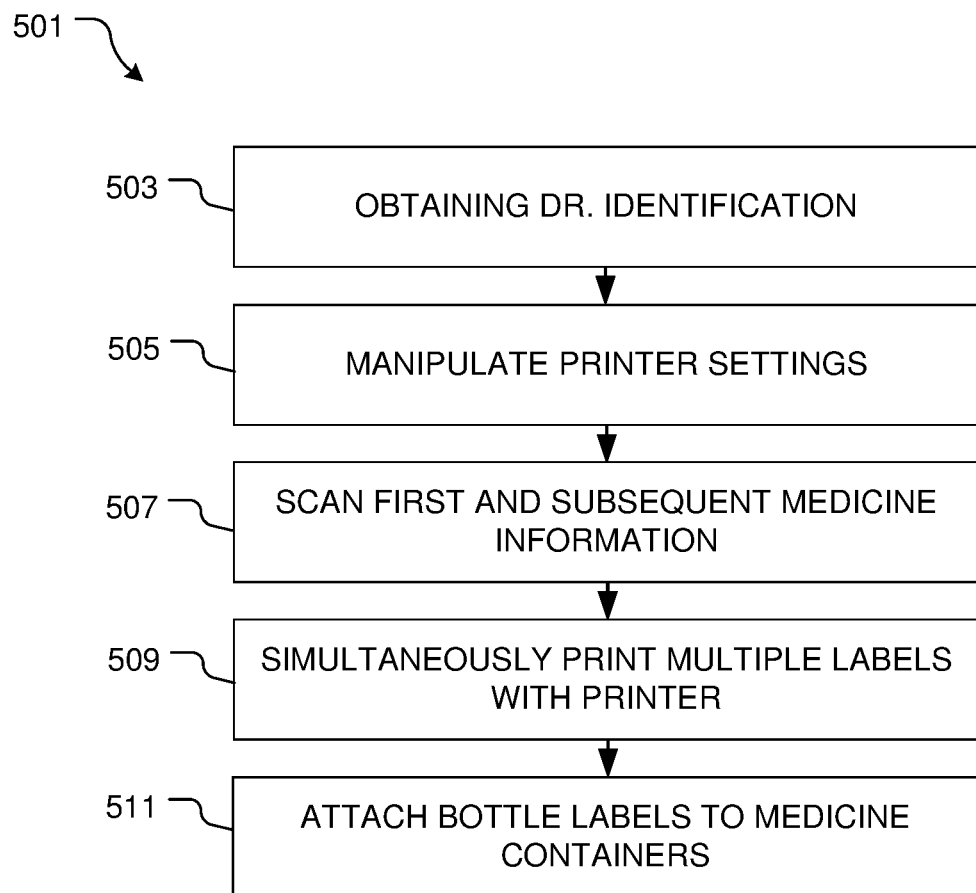
FIG. 5 is a flowchart of the labeling method in accordance with a preferred embodiment of the present application.

In FIG. 5, a simplified flowchart 501 depicting the preferred process is shown. The process starts with obtaining the Doctor's information, which can be achieved via scanner 205, a radio-frequency identification (RFID) badge, or the like, as indicated by box 503. After the Doctor's information is received, the printer settings are manipulated, as indicated by box 505. For example, the user may wish to switch between child and adult medicine dosages, blank labels, and the like. Next, the user scans the barcodes associated with the various types of medicines to be adhered during operation, as indicated by box 507. Thereafter, the printer simultaneously prints the plurality of labels on label sheet 215, as indicated by box 509. Lastly, the individual labels 301 are removed from sheet 303 and placed on bottles 105, as indicated by box 511.

Figure 6:
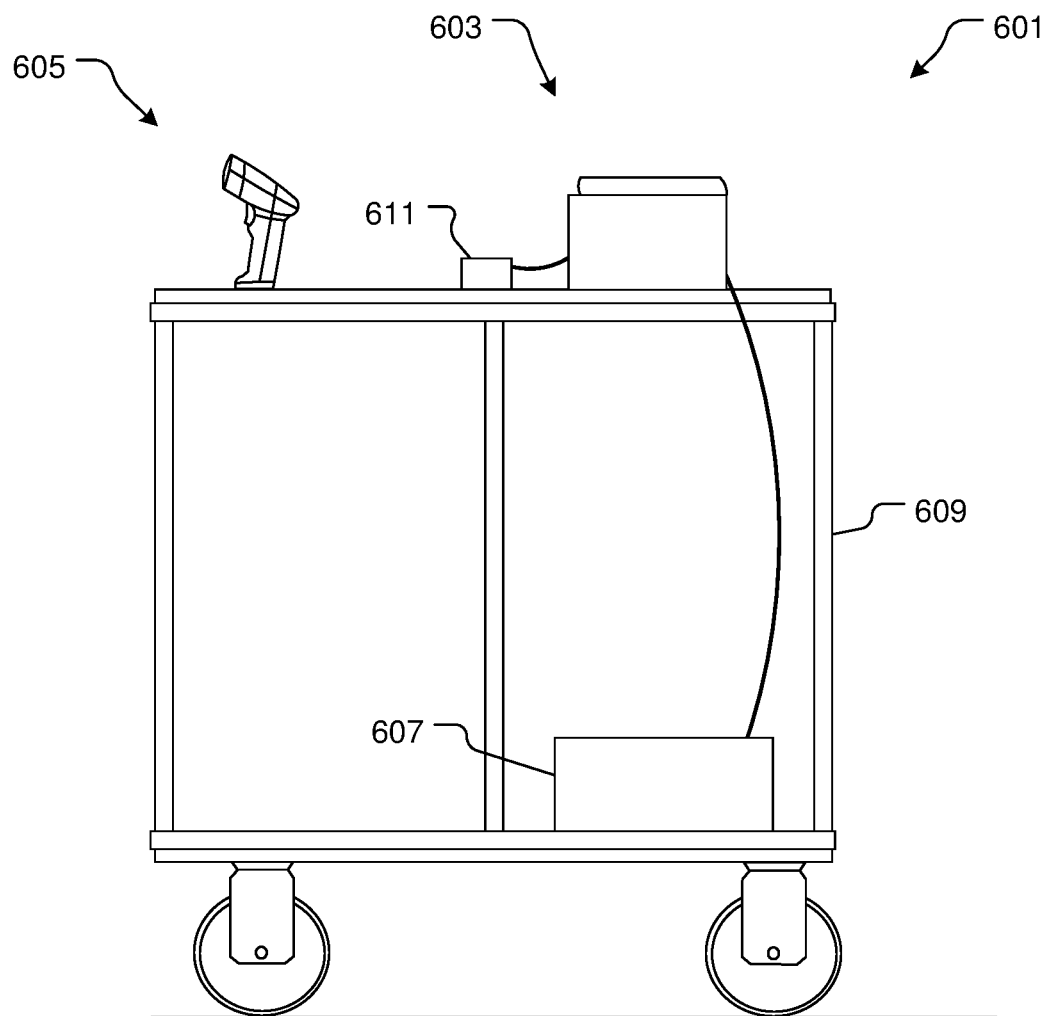
FIG. 6 is a side view of a labeling system in accordance with an alternative embodiment of the present application.

It will be appreciated that alternative embodiments are also contemplated. In FIG. 6, a side view of a printer system 601 is shown in accordance with an alternative embodiment. System 601 is substantially similar in form and function to system 201 and incorporates one or more of the features discussed above, and vice-versa.

System 601 includes a printer 603 operably associated with a wireless scanner 605 and conductively coupled to a battery system 607. As shown, the components of system 601 are carried on a cart 609, which in turn increases the mobility of system 601 during use. One additional feature of system 601 includes a RFID reader 611 configured to wirelessly read information, e.g., the doctor's badge having a RFID tag, during use.

Figure 7:
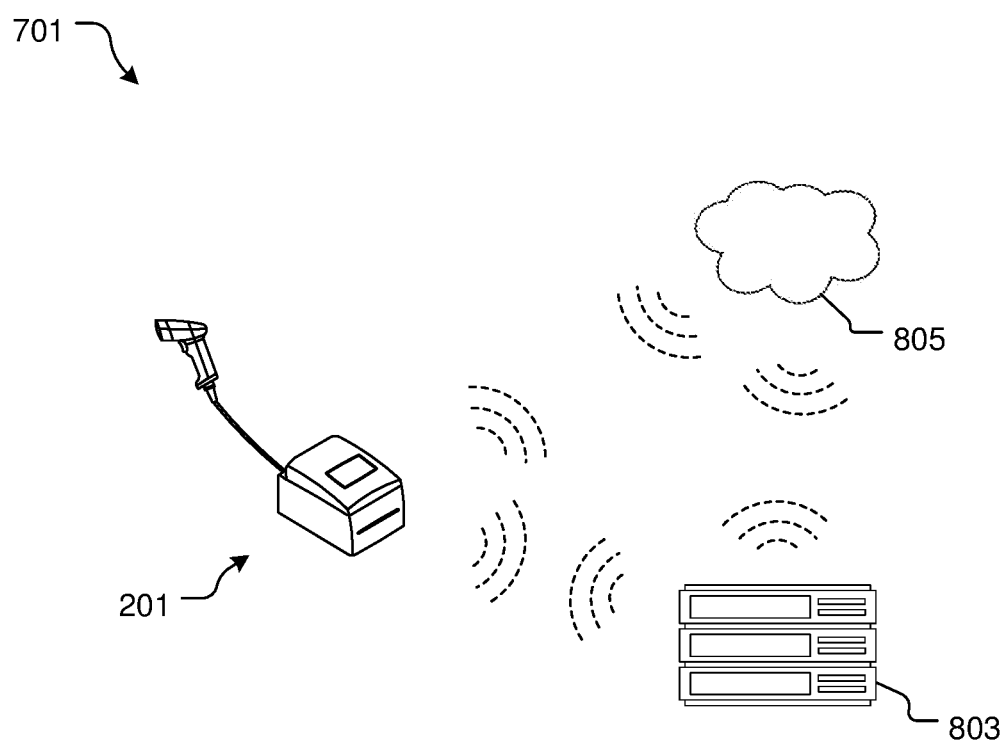
FIG. 7 is a side view of a labeling system in accordance with an alternative embodiment of the present application.

Referring to FIG. 7 in the drawings, a simplified schematic of a labeling system 701 is shown in accordance with an alternative embodiment. System 701 is substantially similar in form and function to the systems discussed above and incorporates one or more of the features discussed herein, and vice-versa.

In the contemplated embodiment, system 701 includes the features of system 201 operably associated with a database 803 and cloud service 805. Accordingly, the data obtained from system 201 can be reviewed and programmed via database 803 and/or cloud service 805. In the exemplary embodiment, the system 201 communicates with database 803 and/or cloud 805 wirelessly. This feature allows the printer to received up-to-date information regarding each type of medicine being used and for other third parties to review the medicines being used by the user during operation. Although not shown, system 201 could include transceivers and other devices that allow communication with database 803 and/or cloud service 805.

Referring now to FIG. 8, a front view of a drug label sheet 801 is shown. In the contemplated embodiment, the drug label sheet 801 contains information about the particular type of drug being administered to the patient. The sheet 801 includes a plurality of boxes, e.g., boxes 803 having information for different types of drugs, which in turn are scanned via scanner 219. After the bar codes are scanned via scanner 219, one or more labels 901 are printed on a sheet, for example, sheet 215 printed by printer 203.

Figure 9:
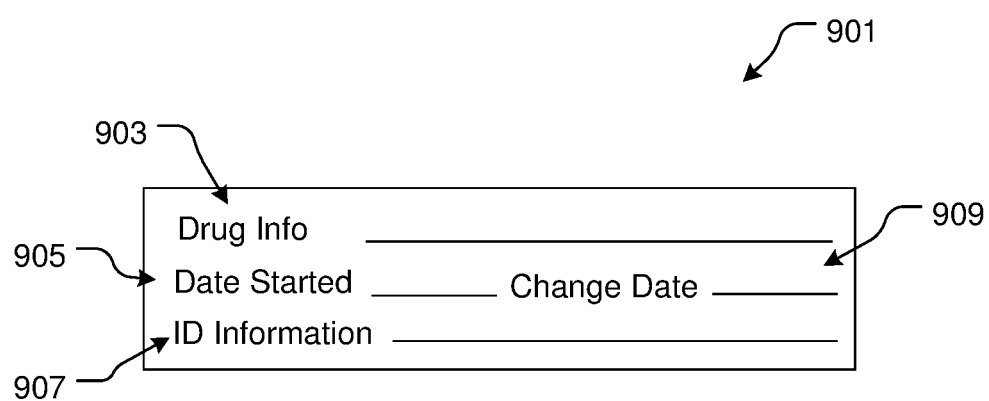
FIG. 9 is a label from a label sheet of the labeling system of FIG. 2.

FIG. 9 illustrates an exemplary label 901 created by scanning box 803. In the exemplary embodiment, the bar code of box 803 provides drug information, which is printed on section 903. The printer is preprogrammed with a date and time, which is printed on section 905. The process discussed above also captures the information from the doctor, nurse, and/or other party administering the drug; this information being printed on section 907.

One of the points of novelty believed characteristic of the process of creating label 901 is providing the change date that the drug being administered needs to changed. For example, it is well known that drugs have an expiration date, which requires the administer to interchange the drug prior to the expiration else the drug becomes useless and/or harmful to the patient. Accordingly, the label 901 has a section 909 that provides the administer the date for drug replacement.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A labeling system for creating labels for medicine containers, comprising:
   a label printer configured to carry a plurality of printing sheets therein, the label printer consisting of:
      a base with a top pivotally attached thereto and forming an interior area to carry the plurality of printing sheets; and
      a display integrally embedded within a top surface of the top and configured to be manipulated by the user;
      an opening extending through the base and into the interior area, the opening configured to provide an exit from the interior area for the plurality of printing sheets; and
      one or more ports for connection with one or more cords;
      wherein the label printer is pre-programmed via a computer, the computer being wholly separate from the label printer;
   a drug administer identification card having a drug administrator barcode printed thereon with an identifying information associated with a drug administrator;
   a card reader configured to read the drug administer identification card and in data communication with the label printer;
   a scanner in data communication with the label printer, the scanner having a reader to scan the drug administer barcode to retrieve the identifying information and a drug barcode; and
   a label sheet printed by the label printer, the label sheet having a plurality of labels adhesively bonded thereto, the label printer being configured to print onto the plurality of labels data information scanned from the administrator barcode and the drug barcode, the label sheet having:
      a first section for a drug name;
      a second section for a dosage;
      a third section for a time and a date;
      a fourth section for the identifying information of the drug administer; and
      a fifth section for a change date, the change date being a predetermined date on which the drug is to be changed;
   wherein a first drug information is printed on a first label of the plurality of labels; and
   wherein a second drug information is printed on a second label of the plurality of labels; and
   wherein information stored on the drug administer identification card is printed on the label sheet.

2. The system of claim 1, further comprising:
   a RFID tag reader operably associated with the label printer, the RFID tag reader being configured to wirelessly obtain the administer information from a RFID tag incorporated into the drug administrator identification card.

3. The system of claim 1, further comprising:
   a drug barcode sheet having a plurality of barcodes for different types of drugs;
   wherein the scanner is configured to scan the barcodes for printing the label sheet via the printer.

4. The system of claim 1, further comprising:
   a cart for carrying the label printer and the scanner.

5. The system of claim 4, further comprising:
   a portable power supply carried on the cart and conductively coupled to the label printer.

6. The system of claim 1, wherein the display is a touchable display manually manipulated by the drug administer.

7. The system of claim 1, further comprising:
   a cloud server in data communication with the label printer; and
   a database in data communication with the cloud server;
   wherein the cloud server obtains information printed via the label printer; and
   wherein the information obtained by the cloud server is stored in the database.

8. A labeling system for creating labels for medicine containers, comprising:
   a label printer configured to carry a plurality of printing sheets therein, the label printer consisting of:
      a base with a top pivotally attached thereto and forming an interior area to carry the plurality of printing sheets;
      a display integrally embedded within a top surface of the top and configured to be manipulated by the user;
      an opening extending through the base and into the interior area, the opening configured to provide an exit from the interior area for the plurality of printing sheets; and
      one or more ports for connection with one or more cords;
   wherein the label printer is pre-programmed via a computer, the computer being wholly separate from the label printer;
   a scanner in data communication with the label printer, the scanner having a reader to scan a drug barcode;
   a drug administer identification card having an RFID tag incorporated therein, the RFID tag programmed with an identifying information associated with a drug administrator;
   a RFID reader in data communication with the RFID tag carried by the drug administer; and
   a label sheet printed by the label printer, the label sheet having a plurality of labels adhesively bonded thereto, the label printer being configured to print onto the plurality of labels data information scanned from the drug barcode and obtained from the RFID tag, the label sheet having:
      a first section for a drug name;
      a second section for a time and a date;

a third section for a change date, the change date being a predesignated date that a drug needs be replaced; and a fourth section for the identifying information of the drug administer via information obtained from the RFID tag.

9. The system of claim 8, further comprising:

a drug barcode sheet having a plurality of barcodes for different types of drugs;

wherein the scanner is configured to scan the barcodes for printing the label sheet via the printer.

10. The system of claim 8, further comprising:

a cart for carrying the label printer and the scanner.

11. The system of claim 10, further comprising:

a portable power supply carried on the cart and conductively coupled to the label printer.

12. The system of claim 8, wherein the display is a touchable display manually manipulated by the drug administer.

13. The system of claim 8, further comprising:

a cloud server in data communication with the label printer; and a database in data communication with the cloud server;

wherein the cloud server obtains information printed via the label printer; and wherein the information obtained by the cloud server is stored in the database.

14. A method to simultaneously print a plurality of drug labels for a plurality of medicine containers, comprising:

providing the system of claim 1;

obtaining identifying information related to a drug administer from a drug administer identification card having a barcode configured to be scanned by a scanner;

storing data of a plurality of information related to different types of drugs in a computer associated with a label printer; and simultaneously printing identifying information related to the drug administer and the plurality of information related to different types of drugs on the plurality of drug labels;

wherein the plurality information related to different types of drugs includes a drug name; a time and a date; and a change date, the change date being a predesignated date that a drug needs be replaced.

15. The method of claim 14, further comprising:

storing the information related to the administer and the plurality of information related to different types of drugs in a database.

* * * * *